United States Patent [19]

Kambara et al.

[11] Patent Number: 5,356,776

[45] Date of Patent: Oct. 18, 1994

[54] DNA MEASURING METHOD

[75] Inventors: Hideki Kambara, Hachiouji; Kazunori Okano, Shiki; Satoshi Takahashi, Kokubunji; Keiichi Nagai, Higashiyamato; Tetsuo Nishikawa, Itabashi, all of Japan

[73] Assignee: Hitachi, Ltd., Tokyo, Japan

[21] Appl. No.: 942,470

[22] Filed: Sep. 9, 1992

[30] Foreign Application Priority Data

Sep. 10, 1991 [JP] Japan .................................. 3-230045
Sep. 18, 1991 [JP] Japan .................................. 3-237757

[51] Int. Cl.$^5$ .............................................. C12Q 1/70
[52] U.S. Cl. ..................... 435/6; 204/182.8; 935/77; 935/78; 436/94
[58] Field of Search ............ 435/6; 935/77, 78, 88; 422/82.08; 204/182.8, 299 R; 436/94

[56] References Cited

U.S. PATENT DOCUMENTS 5,079,169 1/1992 Chu ...................................... 436/172

FOREIGN PATENT DOCUMENTS 0391674 10/1990 European Pat. Off. .

OTHER PUBLICATIONS

Zhang et al Clin Chem (Sep. 1991) 37:1492–1496.
Smith et al Biopolymers (1990) 29:1167–1173.
Urdea et al Nucl Acids Res (1988) 16:4937–4955.

*Primary Examiner*—Margaret Parr
*Assistant Examiner*—Carla Myers
*Attorney, Agent, or Firm*—Antonelli, Terry, Stout & Kraus

[57] ABSTRACT

DNA molecule length can be measured with high precision and efficiency by 1) using such means as electrophoresis gel migration to orient a DNA molecule having a fluorescence label at both its termini into a straight line by its passing through a migration path having in a portion of it an area not more than several micrometers in diameter, detecting the fluorescence label at both the termini at a predetermined location and measuring the interval between the detection of the fluorescence coming from one terminus and that of the fluorescence from the other or by 2) a DNA molecule bound to a fluorescence label at one terminus and to a particle at the other being led as a whole by such means as electric field application into an aperture smaller in diameter than the particle, leaving the particle fixed at the mouth of the aperture to stretch the DNA molecule and detecting the fluorescence position to measure the distance between the bound particle and the bound fluorescence label.

13 Claims, 8 Drawing Sheets

DNA MEASURING METHOD

BACKGROUND OF THE INVENTION

The present invention relates to a method and apparatus for measuring the length of a polynucleotide or biomolecular such as DNA, and is particularly concerned with measuring the length of a not less than 50, especially 100 kilobase long polynucleotide.

Such polynucleotide length measurement is one of the gene analysis means useful in fields like medical chemistry, biochemistry and genetics.

In the past, measuring the base length (or molecular weight) of a long DNA chain has been based on the use of gel electrophoresis migration which provides electric fields in a certain direction. Polyacrylamide gel is effective in separating DNA several bases to 2 kilobases long, and agarose gel is in use for separating DNA 1 to 20 kilobase long.

In conventional electrophoresis using electric fields in a certain direction, molecular sizes are separated in polyacrylamide gel or agarose gel according to the spatial spread of the molecules. To be more specific, the separation is based on whether spatially spread molecules pass through gel meshes. Larger molecules do not pass but become elongated. After all, these elongated molecules are separated according to their shorter diameters. In this case, however, the difference in the size of these elongated DNA molecules is no more than the difference in their seeming lengths. This is why long DNA cannot be separated with molecular sieves. Another conventional technique, pulsed field electrophoresis, varies pulsatively the electric field direction for electrophoresis in agarose gel in order to separate molecules tens of megabases to several megabases long.

A more detailed description of measuring by separation not less than 100 kilobase long DNA may be found in PCT International Publication WO 84/02001 and Nucleic Acid Research, vol. 16, pp. 7563–7582, by B.W. Birren, 1988. In this method, a mixture of giant DNA fragments subject to measurement is injected into wells in an electrolyte-containing gel matrix made of network polymers like agarose, the DNA is allowed to migrate as the direction of electric fields is varied pulsatively, and the DNA is separated according to the size. For instance, when migration is performed for 95 hours in a 0.7% concentration agarose matrix, the direction of 2 V/cm electric fields being varied an angle of +106 degrees with the migration direction every 30 minutes, it is possible to separate 3 to 10 megabase long DNA. The length of the DNA is considered to be measurable on the basis of the bandwidth of the separated DNA with about 10% errors. This pulsed field electrophoresis employs the dependence on elongated molecule lengths of the time taken by varying the direction of the orientation of the molecules by changing the direction of the electric fields (see pp. 364–370, Jikken Igaku, vol. 5 by Hasegawa and Kikuchi (1987)).

The above conventional technique makes it possible to obtain information on the length of very large DNA with pulsed field separation. But the problem is that the longer DNA, the longer time its separation takes. For example, it generally takes 3 or 4 days to separate 3 to 10 megabase long DNA. This conventional technique separates DNA according to the size, namely, the length difference while DNA termini travel through the gel, popping out from and popping in between network molecules composing the gel matrix. Naturally, as the distance of the travel through the gel is shorter, the separation worsens. Moreover, when migration is provided by high electric field intensity, heating impairs separation. Thus it is unfeasible that the conventional technique shortens the analysis time. Since the longer DNA, the longer migration it requires, the technique is not suitable for the practical use for separating not less than tens of megabases long DNA. Besides, the fact that the longer DNA, the longer migration it needs, and the larger bandwidth the separated DNA has deteriorates the precision of the length separation.

Furthermore, the above conventional electrophoresis including pulsed field electrophoresis separates and measures the measurement subject as a group of different molecule sizes, using the difference between molecule sizes and between electrophoresis rates. This deteriorates separation as the molecules are longer, and increases the volume that groups of the same molecule size occupy for a cause such as diffusion, resulting in inefficient separation of long molecules like DNA.

Pulsed field electrophoresis, which varies the electric field direction, uses radio isotope labels or ethidium bromide staining for the purpose of detection. To ensure sufficient detection sensitivity, many molecules (copies) of the same length are necessary and need to be prepared. The resolution for DNA size provided by this technique is not very high because of influences such as molecular heat diffusion, and the molecule length measurement precision is low.

SUMMARY OF THE INVENTION

The present invention, therefore, has as its principal object the provision of a method and apparatus for quickly measuring the base length of biomoleculars having long molecule length like DNA with high measurement precision.

Another object of the present invention is to provide the above-mentioned method and apparatus particularly in the case where only a few molecules (copies) of the same length are available.

A further important object of the present invention is to provide a process and apparatus for quickly measuring the length of not less than 1 megabase long DNA with high measurement precision.

To achieve the above objects, one process in accordance with the present invention labels at least both termini of biomoleculars like DNA with fluorophore, stretches these polymers with electrophoresis having electric fields in a certain direction or with the outflow from apertures to shape them into almost straight lines, transfers them to a buffer solution in which there are no substances like gel causing polymers to migrate at a certain rate irrespective of their length and measures their length. Molecule length is measured by attaching fluorophore labels to both termini of biomoleculars, exciting them with laser beams and then detecting the fluorescence emitted by them.

How to label both termini of a biomolecular like DNA with fluorophore is known. The migration rate of a biomolecular needs only to be less than that rupturing the DNA chain. The upper limit depends on the length of the biomolecular, and can be specified with experiments.

In electrophoresis having electric fields in a certain direction, polymers of large molecule sizes are elongated in the electrophoresis medium, and these polymers oriented in the form of straight lines are transferred to a buffer solution to migrate with their orientation kept straight. The fluorophore labeling both termini of such a biomolecular is irradiated with a laser beam focused into not more than 1 μm at the photodetecting portion and emits fluorescence. The interval between the passing of the fluorescence label at one terminus of the polymer through the portion to which the laser beam has been directed and the passing of the fluorescence label at the other terminus through this portion is measured. Since in a buffer solution where there is no gel a constant electric field intensity causes biomoleculars to migrate at a constant rate, it is possible to calculate the distance between the fluorophore at one terminus of a biomolecular and that at the other terminus from the time the fluorophore labeling both termini of the biomolecular takes to pass through the portion to which the laser beam has been directed and also from the passing rate. This makes it possible to find out the molecule length and base length of DNA. The molecule length can be measured for even 1 molecule (1 copy) by this process. The absence of diffusion, occurring in a measurement of molecule length by molecular migration of a group of many molecules, makes this process capable of measuring molecule length or base length with high precision.

The above-mentioned biomolecular length is measured with length measuring apparatus comprising means for orienting into straight lines the biomolecular subject to this measurement and transferring it, a light source for exciting the fluorophore labeling both termini of a biomolecular, means for detecting the fluorescence emitted by the excited fluorophore and means for measuring the interval between the detection of fluorescence emitted from one terminus of the biomolecular and that of fluorescence emitted from the other terminus. The means for orienting biomoleculars into straight lines and transferring them has means for causing electrophoresis and/or means for causing buffer liquid flow, the biomolecular transfer path having an area up to 10 μm, preferably up to 6 μm, most preferably up to 1 μm in diameter or an area equivalent to these. The provision of an area not more than 10 μm in diameter for the biomolecular transfer path is for the purpose of measuring the length of biomoleculars in terms of each molecule, that is, by drawing the DNA molecules one by one.

To achieve the objects of the present invention, another process binds a label to one terminus of DNA, fixes the other terminus to a matrix physically or chemically, stretches the DNA by means of electric fields or liquid flow and detects the position of the terminus bound to the label to measure the length of the DNA. In this manner, the length of DNA is measured for each molecule by stretching the DNA with an external force and measuring the distance between the two termini of a molecule. Here, it is not always necessary to stretch DNA fully and measure its absolute length. Since fluctuations due to thermal vibration occur to longer DNA, it is unfeasible to stretch it to the full. This difficulty can be overcome by obtaining a calibration curve from DNA whose lengths are known and then finding the length of the DNA subject to the measurement. To fix DNA, only one terminus needs to be used so that the DNA can be stretched with certainty. Materials like nitrocellurose film or nylon inducer conventionally in wide use for hybridization cannot be used because they fix DNA at more than one point.

Figure 8:
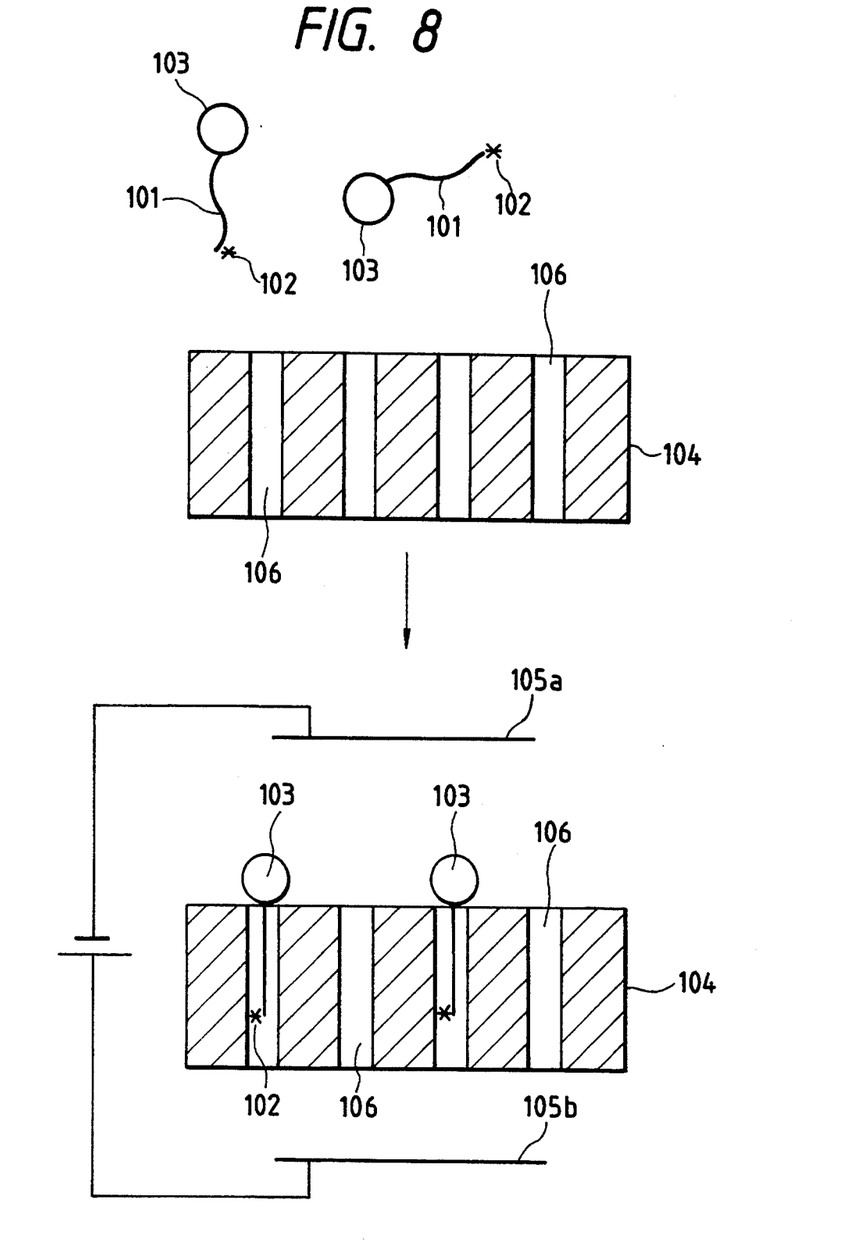
FIG. 8 is a schematic illustration of the second principle of measuring the length of biomoleculars such as DNA according to the present invention.

For example, as shown in the scheme in FIG. 8, one terminus of DNA 101, which is subject to length measurement and bound to a label 102 at the other terminus, is bound to a particle 103 whose diameter is about 0.2 μm or 10 μm, preferably 0.2 μm to 6 μm, most preferably 0.2 μm to 1 μm. Then, this DNA bound to the particle 103 is led to a matrix 104 having apertures 106 passable to DNA 101 but not to the particle 103. The DNA can pass one of the apertures 106 except its portion bound to the particle 103, which allows one terminus of the DNA to be fixed in a specific position. Applying electric fields between electrodes 105a and 105b or using liquid flow causes DNA to migrate, fixes the particle 103 at the mouth of the apertures and stretches the DNA. The label is searched for along the apertures 106, and it is detected that the label 102 is in a position corresponding to the particle 103 at the fixed terminus.

To bind a particle to the DNA terminus to be fixed, such methods using a bifunctional reagent as the carbodiimide method (this will be described later in connection with the first example of the present invention), the glutaric aldehyde method and the N-succinimidyl 3-(2-pyridyldi​tio) propionate method (SPDP) can be employed to bind a particle to primer having an amino group, and then the ligation method can be employed to bind the particle to the subject DNA. As the particles to be bound to the fixed terminus of DNA, latex particles or acryl-like particles are used. The other terminus of the DNA can be bound to a label such as fluorophore by the ligation method which is known. The matrix to be fixed to DNA at a terminus is produced by employing semiconductor processing techniques such as electron beam processing or sputtering to form in quartz glass or a silicon wafer apertures not less than 0.1 μm in diameter and smaller than the diameter of the particle to be fixed. The diameter of apertures are not less than 0.1 μm, since the lower limit of production processes is 0.1 μm.

According to the present invention, one terminus of DNA is fixed, the DNA is stretched by applying an external force to it, and then the distance between the fixed terminus and the other terminus is measured. The terminus opposite to the fixed one is bound to a label such as fluorophore or an enzyme. The position of the fixed terminus, in a case such as where DNA bound to a particle is fixed to an aperture, can be specified in advance because the positions of the apertures are known. This position can also be specified by binding a label to the fixed terminus as well as the other terminus. The other terminus bound to a label can be found out by detecting fluorescence if the label is fluorophore or by measuring oxygen activity if the label is oxygen. For instance, 1 megabase long double helical DNA measures about 0.34 mm when stretched. Since the fixed terminus and the label measure not more than 1 μm, it is easy to recognize the fixed terminus of DNA and the other terminus bound to a label both separated from each other. Thus the length of DNA can be measured for each molecule.

The intensity of electric fields to be applied for stretching DNA needs to be not less than 40 V/cm to 50 V/cm such that the DNA cannot be ruptured. The detection of label fluorophore positions can be performed by changing the location to which the laser beam is directed.

The use of an enzyme as a label bound at one terminus of DNA for detection is possible by this method: binding alkaline phosphatase to one terminus of DNA by the SPDP method, applying this terminus to a chemiluminescent assay using 3-(2'spiroadamantane)-4-methoxy-4-(3"-phosphoryloxy)-phenyl-1, 2-dioxetane (AMPPD) as the substrate and then detecting emission points with a CCD camera or a camera equipped with an image intensifier.

DESCRIPTION OF THE PREFERRED EMBODIMENTS

Figure 1A:
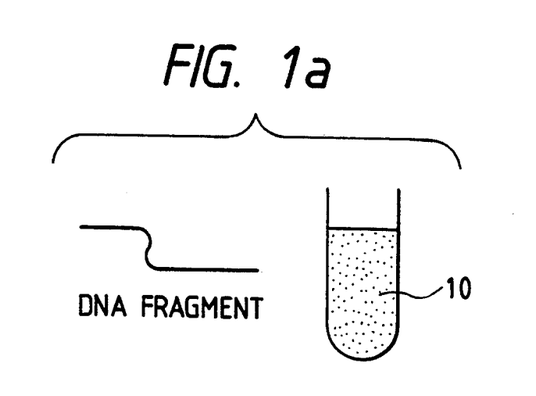
FIGS. 1a and 1b are schematic illustrations of the first principle of measuring the length of biomoleculars such as DNA according to the present invention.
Figure 1B:
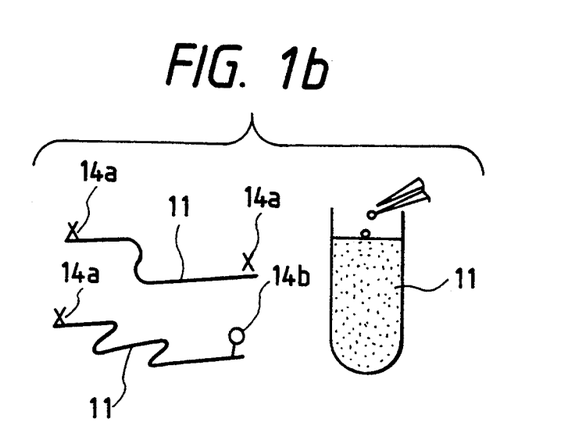
Figure 2:
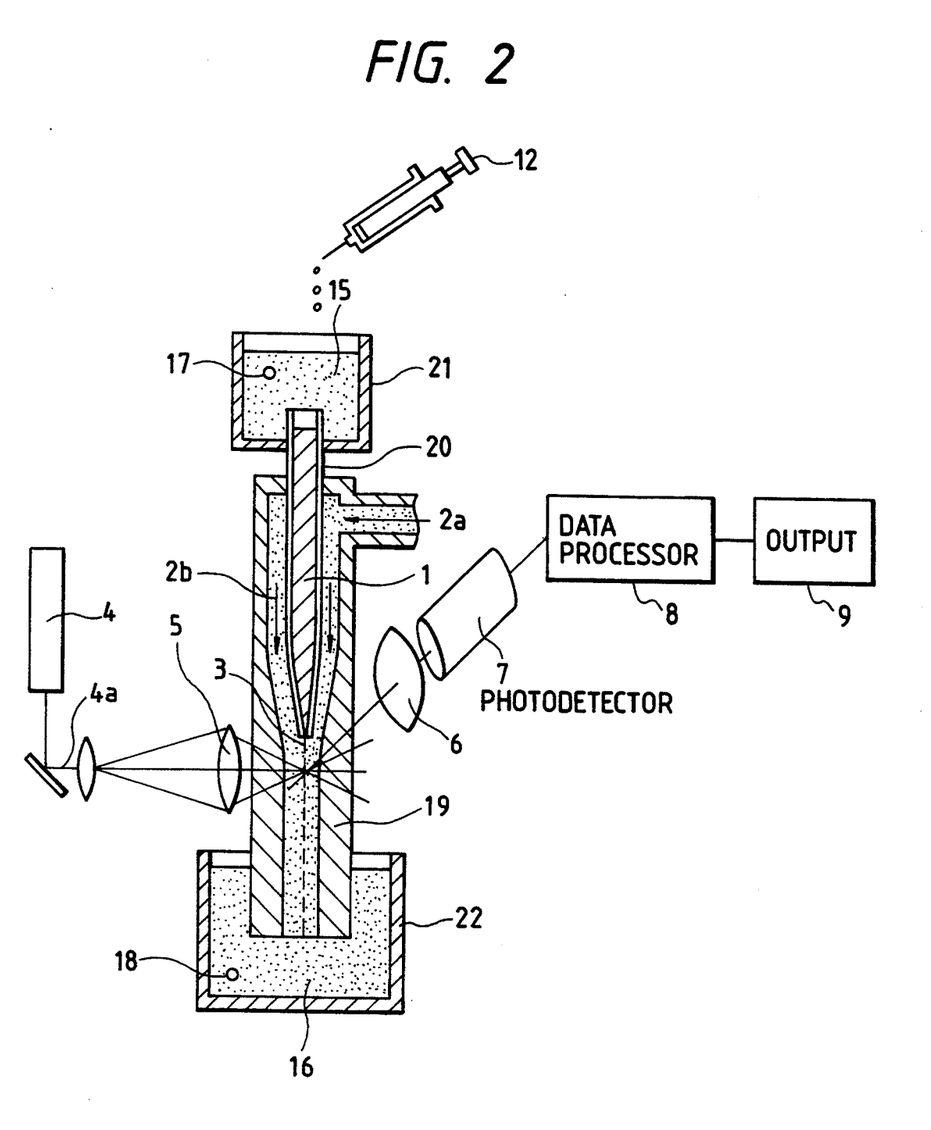
FIG. 2 is a sectional view of an embodiment of the present invention illustrating an apparatus for measuring the length of biomoleculars such as DNA.

Referring now to FIGS. 1a, 1b and 2, the fundamentals of embodiments of the present invention in which both termini of DNA are labeled with fluorescence will be described. FIG. 1a illustrates the digestion of DNA with an enzyme, FIG. 1b the fluorescence labels at DNA termini. These FIGS. 1a and 1b show the principle of biomolecular length measurement, such as DNA molecule length measurement, of the present invention. To take DNA molecules as an example, the principle of biomolecular length measurement of the present invention will be sketched as this procedure: (1) digesting DNA molecules with enzymes (FIG. 1a), (2) binding fluorescence labels to the termini of digested DNA to produce DNA fragment molecules whose termini have been labeled with fluorescence (FIG. 1b), (3) injecting the fluorescence-labeled DNA fragment molecules into an upper buffer solution 15 (FIG. 2) and applying them to electrophoresis in the gel to orient the DNA fragment molecules into straight lines, (4) transferring DNA fragment molecules from the electrophoresis agarose gel migration path outlet not more than 1 $\mu$m in diameter to a buffer solution with their orientation kept straight. Incidentally, the lower limit of the diameter of the outlet, that is, the outflow part of the electrophoresis migration path virtually depends on the limit of production processes, (5) directing a very thin laser beam to the DNA fragment molecules not away (not more than 1 mm) from the electrophoresis migration path outlet, (6) receiving the fluorescence coming from the DNA fragment molecule termini labeled with fluorescence by using the laser beam, and detecting it with a photodetector 7 (FIG. 2), using clocking means to measure the time the fluorescence at both termini of the fluorescence-labeled DNA fragment molecules takes to pass through the above-noted portion to which the laser beam has been directed and obtaining the length of the DNA fragment molecules from the measurement results and the flow rate of DNA molecules.

EXAMPLE 1

Figure 3:
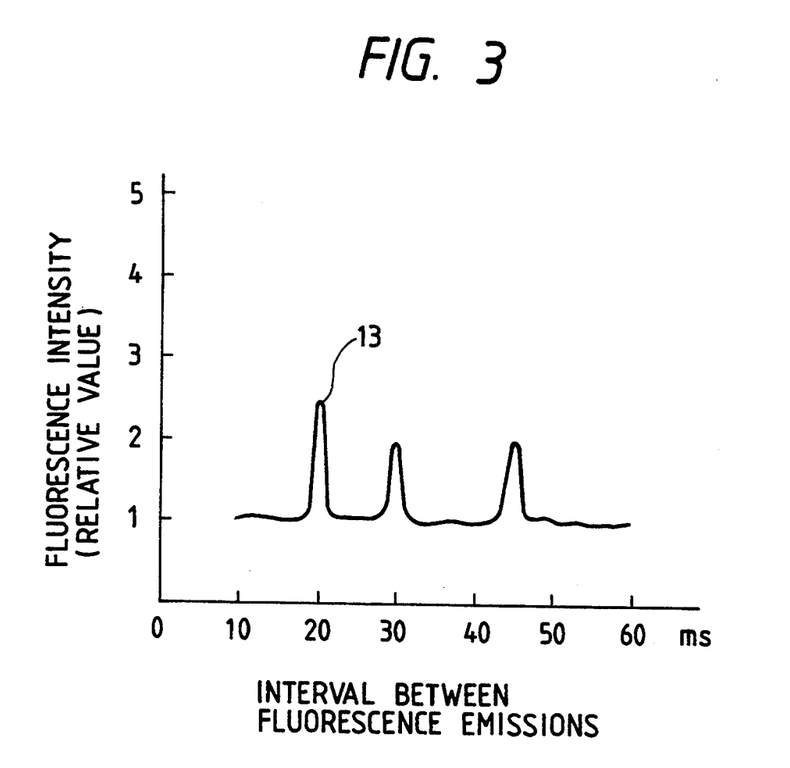
FIG. 3 is a graph of fluorescence detection intervals resulting from the measurement in an embodiment of the present invention.

Now, an example of the present invention will be described in detail. (1): First, in the sample solution 10 of the DNA molecules to be measured for length and base length, a restriction enzyme (e.g., Not I) is used for causing a characteristic chemical reaction in each base portion (FIG. 1a) so as to digest the DNA into a plurality of DNA fragment molecules (FIG. 1a). (2): An enzyme (ligase) is used for binding the termini of these digested DNA fragments to DNA oligomers having fluorescence labels 14a and 14b so as to obtain a labeled DNA sample 11 (FIG. 1b). When a restriction enzyme is used for binding fluorescence-labeled DNA oligomer in the form of double strands to the termini of the DNA digested with the restriction enzyme, one or more than one piece of fluorophore are introduced into each double strand of DNA. Not less than two fluorophore molecules can be bound to one terminus of digested DNA. For the fluorophore, FITC (fluoreceine isothiocyanate: 525 nm maximum emission wavelength) or Texas Red (615 nm maximum emission wavelength) can be used. (3): When the DNA fragment molecules 11 whose termini both have been labeled with fluorescence are injected with a sample injector 12 shown in FIG. 2 into an upper buffer solution 15 of apparatus shown in FIG. 2 for measuring the length of polymers like DNA, and they migrate in electrophoresis in the agarose gel in a capillary tube 20, the DNA fragment molecules 11 whose termini have been labeled with fluorescence stretch in the direction of the migration and are oriented in the form of straight lines. The diameter of the capillary tube electrophoresis portion may be the conventional size, 50 $\mu$m to 100 $\mu$m or more than that. Since orienting the DNA fragment molecules is the chief objective here, the length of the area having agarose gel in the molecular orientation migration portion 1 is 1 cm, migration length in general being not less than 1 cm. But to separate the DNA fragment molecules roughly, 5 cm or more is a suitable migration distance. (4): If the outlet (portion for sample elution) of the electrophoresis agarose gel migration path is in the form of a capillary tube whose inside diameter is not more than 6 $\mu$m, and there is liquid flow 2b for sheath flow provided by supplying a buffer solution through a buffer solution inlet 2a and an electric field provided by an upper electrode 17 and a lower electrode 18, a flow path 3 for oriented DNA from the outlet where the labeled DNA sample molecules 11 pass in an area not more than 1 $\mu$m in diameter with their orientation kept straight can be formed in a sheath flow forming tube 19. Incidentally, one end of the agarose gel is in contact with an upper buffer solution 15 in an upper buffer vessel 21, the migration being caused by the upper electrode 17 and also the lower electrode 18 in a lower buffer vessel 22 filled with a lower buffer solution 16. (5): A very thin laser beam 4a is directed to the flow path 3 for oriented DNA not away (not more than 1 mm) from the above-noted outlet of the electrophoresis migration path so as to excite the fluorophore at one of the two termini of the DNA fragment molecules 11 whose termini both have been labeled with fluorescence. For the light source 4 of the laser for exciting the fluorophore, either the Ar ion laser (488 nm, 10 mW) or He-Ne Laser (594 nm, 3 mW) are suitable, but this example employs a combination of Texas Red and He—Ne laser used as the fluorophore and the laser light source respectively. He—Ne laser is thinned into not more than 1 $\mu$m with the laser beam thinning lens 5 and directed to the flow path 3 for oriented DNA. Then, the fluorescence sent out by the fluorescence-labeled DNA fragment molecules 11 is detected from the direction almost at right angles with incident angle of the laser beam. The presence of DNA fragment molecule termini in the area of 1 ($\mu$m)$^3$ means that at least 2 pieces of fluorophore are included in the volume of 1 ($\mu$m). This corresponds to a concentration of $3 \times 10^{-9}$M which sends out much stronger light than the background light (usually weaker than $3 \times 10^{-11}$M fluorophore). (6): The flow rate of DNA on the flow path 3 for oriented DNA depends on the electric field intensity, but in this example the DNA flow rate for 25 V/cm electric field intensity is about 3 mm per second regardless of DNA length (Bio/Technology, vol. 6, pp. 816-821 (1988)). The fluorescence-labeled DNA fragment molecules 11 take about 0.3 ms to pass through the portion to which the laser beam has been directed. In the meantime the fluorophore emits about $6 \times 10^4$ fluorescence photons. These fluorescence photons pass through a light receiving lens 6 and a filter (not shown in the drawings) and are detected with a photodetector 7. In this example, the light receiving efficiency of the light receiving system for the emitted fluorescence is about 5%, and the photoelectric transducing efficiency of the photodetector 7 is about 5%. In other words, since about 150 entities of fluorescence are countable among those emitted during the passing of fluorophore through the detection portion, the time that the passing takes can be obtained accurately. The number of photons for measurement can also be increased to about 1000 by adding to the amount of laser emission, the amount of fluorophore for labeling or the efficiency of light receiving. This makes it possible to take a more detailed measurement of the time that the passing takes. Using clocking means to obtain the time between the passing of one terminus of DNA through the portion to which the laser beam has been directed and the passing of the fluorescence label at the other terminus through this portion can calculate the length of the fluorescence molecule with the help of the above-noted DNA flow rate. The processing of required data is performed by a data processor 8, and results of this processing are issued from output 9. FIG. 3 shows an example of a measurement result according to the present invention. The x-axis is used for the interval between two signals, namely, the interval between the fluorescence emission from the fluorophore at one terminus and that from the fluorophore at the other terminus of the fluorescence-labeled DNA fragment molecules 11, and the y-axis for counts of the fluorescence photons emitted by the DNA fragment molecules 11. In this example, flow takes 0.3 ms to travel 1 $\mu$m, so the period 1 ms corresponds to about 10 kilobase long DNA. A signal 13 resulting from the labeled DNA samples 11, which is shown in 13, represents labeled 200 kilobase long DNA samples. When the labeled DNA samples 11 have comparatively many molecules (copies), the interval is obtained between the fluorescence emission from the fluorescence label at the rear terminus of the first DNA molecule (the fluorescence from the front terminus from the first DNA molecule has already been measured) and the fluorescence emission from the fluorescence label at the front terminus of the second DNA molecule. This time is random and has a greater distribution. On the other hand, the interval between the occurrence of a fluorescence signal resulting from the fluorescence label at the front terminus and that from the fluorescence label at the rear terminus of one labeled DNA sample molecule 11 is invariably dependent upon the length of the fragment, so accumulating the time data gives a peaked distribution and obtains the lengths of DNA fragments. Obviously, it is also possible to obtain them from one DNA fragment molecule (one copy).

EXAMPLE 2

Figure 4:
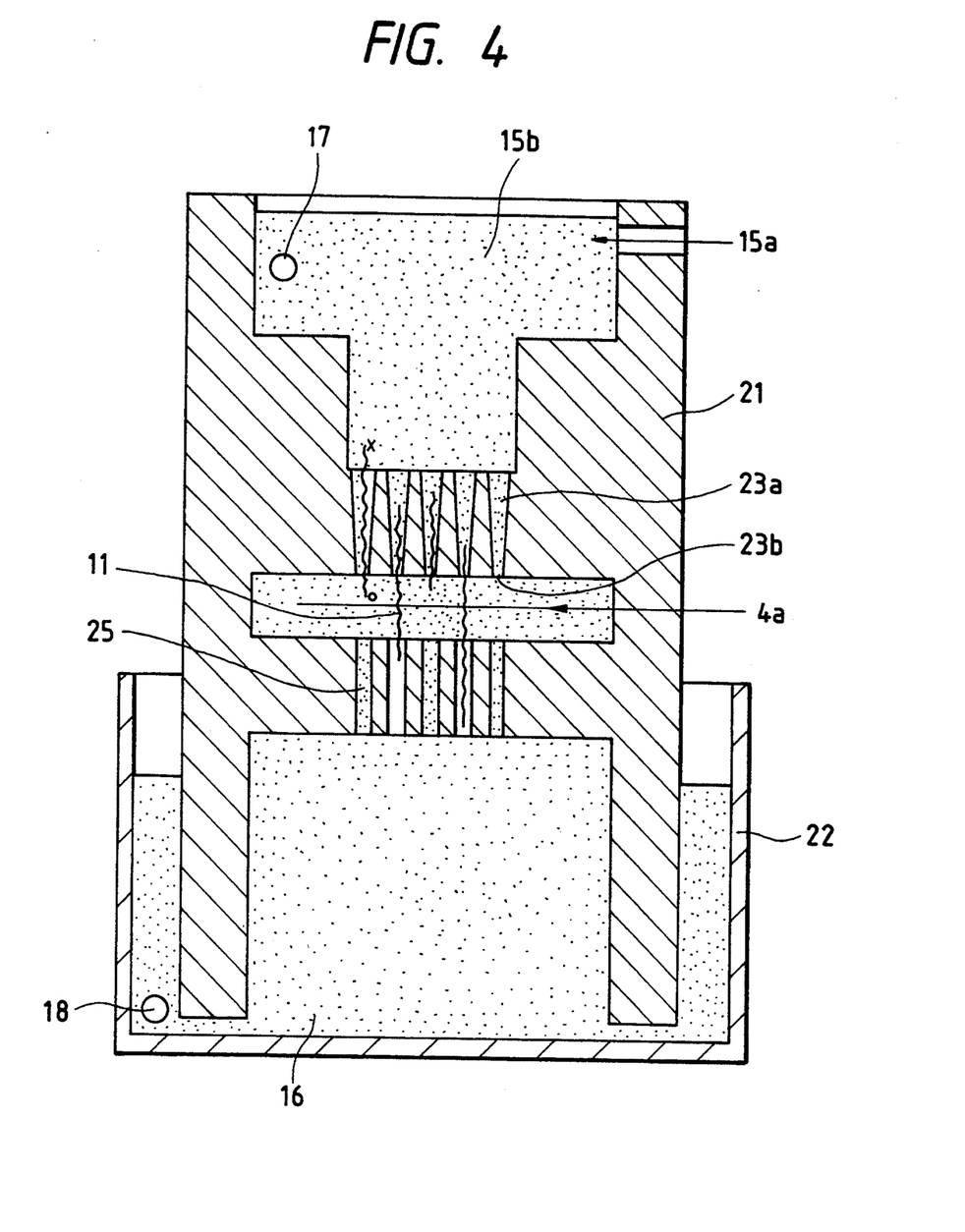
FIG. 4 is a sectional view of another embodiment of the present invention illustrating an apparatus using capillary tubes to measure the length of biomoleculars such as DNA.

In the above example, electrophoresis agarose gel migration and sheath flow are used for the formation of the flow path 3 for oriented DNA on which DNA fragment molecules pass with their orientation kept in the form of straight lines. But the straight-line orientation can be achieved by drawing biomolecules out of a capillary tube with electric fields and buffer solution flow. FIG. 4 illustrates an example of such apparatus. Fluorescence-labeled DNA samples 11 are injected from an upper buffer solution inflow opening 15a. Upper buffer solution 15b is supplied to an upper buffer vessel 21. The path where a laser beam 4a goes and a lower buffer vessel 22 are filled with a lower buffer solution 16. To cause samples to migrate, voltage is applied to an upper electrode 17 and a lower electrode 18. The upper buffer vessel 21 is equipped with sample spewing capillary tubes 23a whose bottoms are spewing outlets 23b smaller (not more than 6 $\mu$m) in diameter than the tops, and is also equipped with sample passing capillary tubes 25 whose inside is not more than 6 $\mu$m in diameter. The electric field provided by the upper electrode 17 and the lower electrode 18 and the flow of a buffer solution formed with the spewing capillary tubes 23a make it possible to orient the fluorescence-labeled DNA samples 11 into straight lines and draw them out of the spewing outlets (spewing outlet portion) 23b and to forcibly orient the fluorescence-labeled DNA samples 11 through the sample passing capillary tubes 25. The laser beam 4a is directed to the proximity of the spewing outlets 23b (not more than about 1 mm from the outlets), and the fluorescence emitted from the spewed labeled DNA is detected from the direction almost perpendicular to the surface of the FIG. 4 page, or from the bottom of the lower buffer vessel 22. The optical system for fluorescence excitation and detection is the same as in FIG. 2.

EXAMPLE 3

Figure 5:
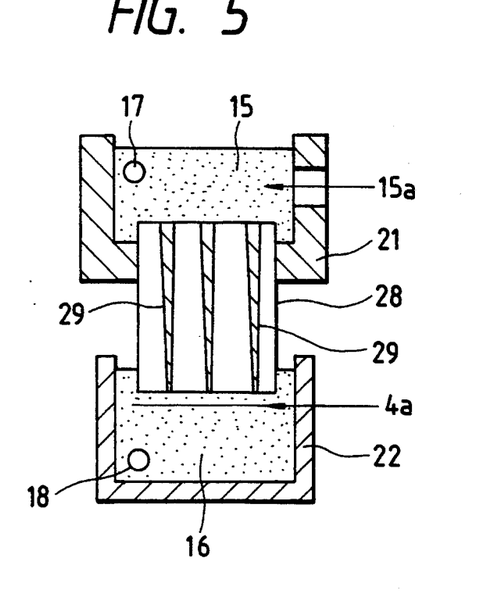
FIG. 5 is a sectional view of still another embodiment of the present invention illustrating an apparatus using fine grooves to measure the length of biomoleculars such as DNA.

In the same manner as the drawing of samples out of capillary tubes shown in FIG. 4, it is possible as shown in FIG. 5 to draw biomoleculars out of fine grooves and orient them into straight lines by using electric fields and a buffer solution 15a. To be more specific, DNA molecules can be oriented by causing them to flow out from a group of fine grooves 29 whose width and depth are about 1 μm, a little larger than the shorter diameter of DNA molecules (and which are made of two plates 28 of such material as silicon crystal or glass). The width and depth of the fine grooves 29 can be not more than 1 μm. Tapering the fine grooves 29 made of two plates 28, namely, flow paths for oriented DNA can strengthen the electric field intensity and stretch DNA more, resulting in the migration of samples oriented in the form of straight lines. Such flow paths for oriented DNA can be provided by a semiconductor pattern formation technique such as grooving the surface of silicon crystal plates or glass materials or a processing technique such as etching.

EXAMPLE 4

Figure 6:
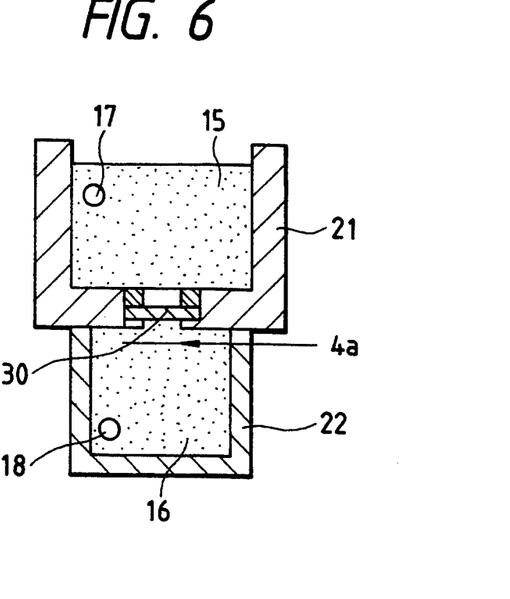
FIG. 6 is a sectional view of a further embodiment of the present invention illustrating an apparatus using a molecular sieve to measure the length of biomoleculars such as DNA.

As shown in FIG. 6, it is possible to measure the length of molecules like DNA by means of electrophoresis using electric fields and a molecular sieve 30 to spew samples out of the molecular sieve. For the molecular sieve 30, such products as the OMEGA Cell by Filtron Inc. in the U.S. can be used.

In the examples shown in FIGS. 5 and 6, as in FIG. 4, fluorescence labels are excited with the laser beam 4a, and the excited fluorescence is detected from the direction almost perpendicular to the surface of the drawing page, or from the bottom of the lower buffer vessel 22.

In the above examples, the combination of Texas Red fluorophore having a single maximum emission wavelength and He—Ne laser is used But it is also possible to digest DNA molecules with more than one restriction enzyme and also to label both termini of DNA fragment molecules with fluorophore having emission wavelengths different to each other terminus so as to detect these termini separately according to their wavelengths. In this case, the fluorescence label primer (in the form of double strands) capable of junction with both termini of double-stranded DNA is bound to both termini by the ligation method enzyme reaction.

It is also possible to use as labels minute particles which have adsorbed and are bound to fluorophore and thereby to label both termini of biomoleculars with one kind or different kinds of fluorophore. As such minute particles the latex particles by Ployscience, Inc. can be used which are 0.1 μm in diameter and contain a coumarin-like coloring matter and have carboxyl groups on the surface.

Since DNA with a double helix is about 3.4 Å long for 1 base, it is about 1 μm long for 3 kilobases. Laser beams, if their convergence conditions are optimized, can be thinned into about 0.5 μm. Thus the length of DNA can be measured to a precision of 1 to 2 kilobases.

Reducing the diameter of the directed laser beam to the quantity equal to its wavelength or a smaller one by such means as fiber can increase the precision of DNA length measurement.

Figure 7:
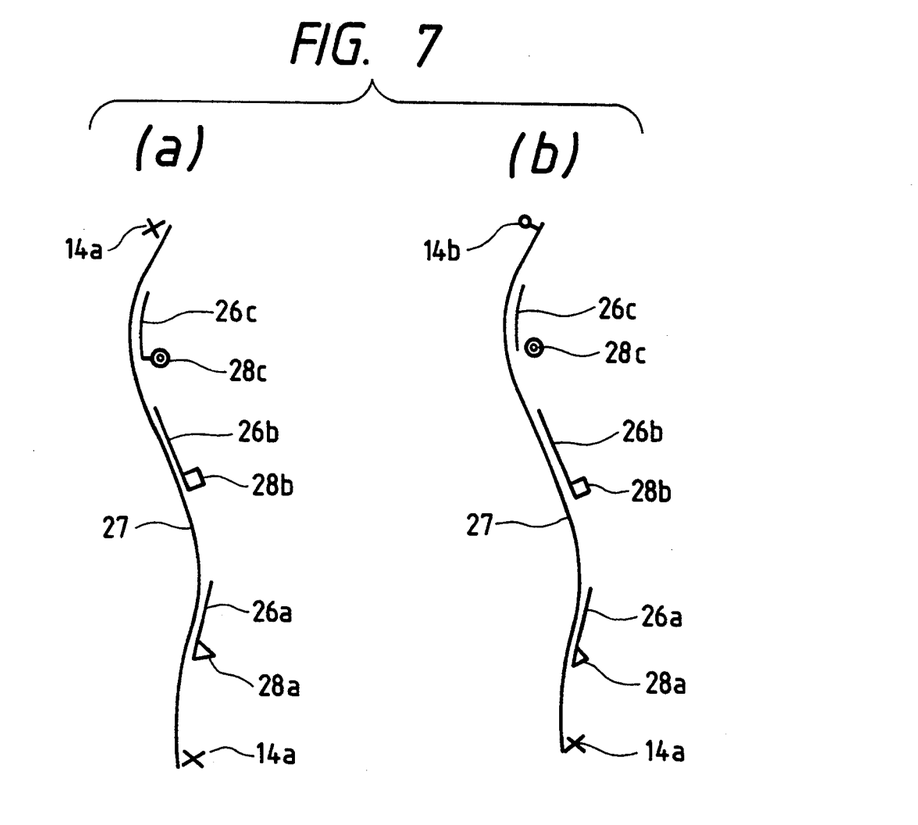
FIG. 7 is a schematic representation of the structure of single-stranded DNA whose termini both are labeled with fluorescence and which is bonded through hybridization to fluorescence-labeled DNA probes at other locations.

The measurement of DNA length has been described so far. According to this process, as shown in FIG. 7, it is also possible to produce a detailed DNA map by binding both termini of single-stranded DNA 27 to fluorescence labels 14a and 14b of different kinds or to fluorescence labels 14a and 14a of the same kind, forming more than one DNA probe 26a, 26b and 26c having fluorescence labels 28a, 28b and 28c at various locations and a hybrid, orienting the DNA into a straight line, causing it to migrate and detecting the fluorescence labels 28a, 28b and 28c sequentially with the apparatus described earlier.

As understood from the above, according to the present invention relating to labeling both the termini of a biomolecular with fluorescence and then measuring its length, a measurement is taken with the DNA molecules stretched, i.e., oriented into straight lines, so the advantage is that the precision is higher than the conventional method of separating lengths of DNA according to the difference in the spread of DNA molecules, and that the length of DNA molecules can be measured by using fewer DNA molecules. The measurement precision is 1 to 2 kilobases, so it is possible to measure tens of kilobases to hundreds of kilobases long DNA or DNA longer than that. This precision is tens of times as high as that by conventional methods.

According to the present invention, in addition to DNA length measurement, it is also possible to produce a detailed DNA map by forming fluorescence label DNA probes and a hybrid at various locations other than the termini in single-stranded DNA, orienting the DNA into a straight line, causing it to migrate and then detecting labels.

Now, an example will be described in which one terminus of DNA 101 is bound to a label 102 such as fluorophore, the other terminus is physically or chemically fixed to a matrix 104, the DNA is stretched by means of electric fields or liquid flow, the position of the terminus bound to the label is detected, and then the length of the DNA is measured.

First, DNA is stretched with an external force, the distance between the termini is measured, and the length of the DNA is measured for each molecule. Here, it is not always necessary to stretch DNA fully and measure its absolute length. Since fluctuations due to thermal vibration occur to longer DNA, it is unfeasible to stretch it to the full. This difficulty can be overcome by obtaining a calibration curve from DNA whose lengths are known and then finding the length of the DNA subject to the measurement. Incidentally, it is known that in general when DNA is fully stretched, it is 0.21 nm long for each base. To fix DNA, only one terminus needs to be used so that the DNA can be stretched with certainty. Materials like nitrocellurose film or nylon inducer conventionally in wide use for hybridization cannot be used because they fix DNA at more than one point.

As shown in FIG. 8, one terminus of DNA 101 subject to measurement and having a label 102 at the other terminus is bound to a particle 103 whose diameter is about 0.2 μm to 10 μm. In fact since this particle needs to be sufficiently smaller than the DNA length, its size is up to 10 μm, more preferably up to 6 μm, most preferably up to 1 μm. The apertures for capturing the particle are at least about 0.1 μm in size. Thus the particle size may be at least 0.2 μm. The DNA bound to the particle 103 is passed through the matrix 104 having apertures through which the particle 103 cannot pass. The DNA can pass one of the apertures 106 except its portion bound to the particle 103, which allows one terminus of the DNA to be fixed in a specific position. It is possible then to fix the DNA to the matrix 104 and stretch it with the help of the particle 103 by applying electric fields between electrodes 105a and 105b or using liquid flow. In this process, the length of DNA is found by detecting that the label 102 is in a position corresponding to the fixed terminus. Using a container having grooves or apertures not passable to the particle 103 fixes the particle 103 to the mouths of the grooves or apertures, and stretches the DNA along the grooves or apertures provided in a certain direction. A search for the label 102 therefore needs to be made only along the grooves or apertures. Naturally, gel matrices can be used for fixing the particle 103 and stretching the DNA. In this case, the particles 103 are captured at the mouths of the gel matrices, and the DNA main portion and the label 102 stretch inside the gel matrices. In addition, the distance between one DNA terminus fixed with the fixing particle 103 and the label 102 at the other terminus can be measured by using the fixing particle 103 as the label specifying an origin. The DNA subject to measurement can be fixed also by means of association reaction. One terminus of the target DNA is bound to primer DNA whose series is known, and this terminus is allowed to fuse through hybridization with a matrix bound to DNA primer complementary to the primer whose series is known, resulting in fixing the DNA bound to a label. In this case also, the length of DNA can be measured, the DNA being stretched by such means as electric fields. Instead of complementary DNA chains, biotin-avidin association reaction or immunoreaction can be used. Now, Examples 5 and 6 of the present invention will be described in detail.

EXAMPLE 5

The measurement subject is DNA prepared from human leucocytes. A DNA fragment was digested with the Sfi I restriction enzyme and bound to coloring matters such as fluorescein-system, 4-nitrobenz-2-oxa-1, 3-diazole-system, rhodamine-system, phthalocyanine-system, phycobiliprotein inducer and a 1 μm particle. Then, the distance between its termini is measured using a confocal laser scanning microscope. From now the procedure for this will be described in reference to FIGS. 9 and 10.

Figure 9:
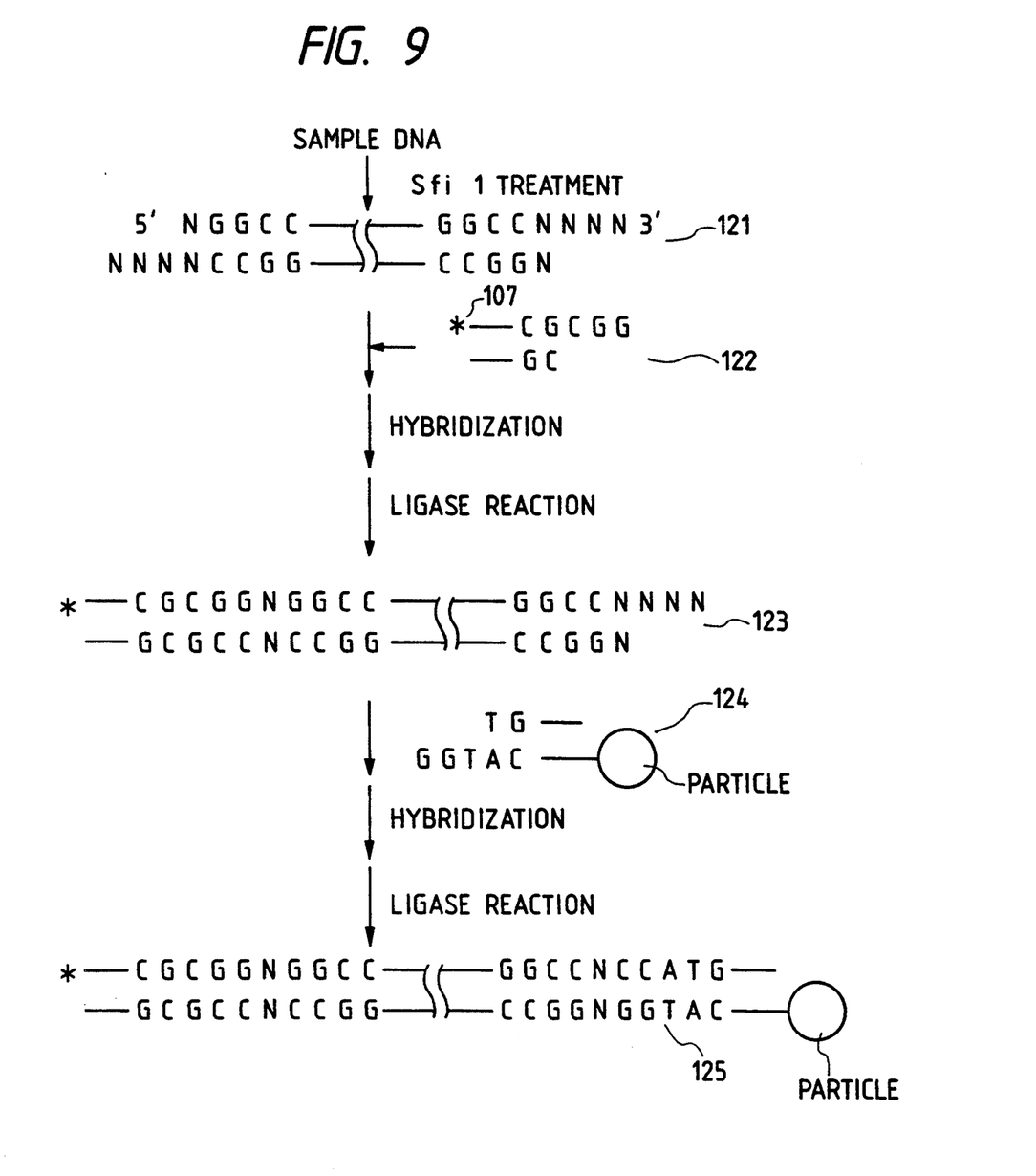
FIG. 9 is a schematic representation of another embodiment of the present invention illustrating an apparatus for preparing a DNA fragment.

Referring to FIG. 9, preparing a DNA fragment having one terminus bound to fluorophore and the other to a fixing particle will be described. First, human whole blood drawn and injected into a blood collecting tube containing heparin is centrifuged with Ficoll-Paque to obtain leucocytes. These leucocytes are cleaned in 5 mM phosphoric acid buffer (pH 7.4) containing 75 mM NaCl and 25 mM EDTA, and kept at 50° C. for 3 hours with 0.5M EDTA, 1% N-lauryl sarcosine and 0.5 mg/ml protease K added to them. Substances like protein are extracted and removed with a mixture, say, of chloroform and phenol in equal proportions. RNA is decomposed with RNase, and then ethanol is added to obtain DNA. The DNA is dissolved in 10 mM Tris HCl buffer (pH 8.0) containing 1 mM EDTA, and dialyzed against the buffer. The resulting human DNA is kept at 50° C. with 0.1 mg/ml cattle serum albumin, 7 mM 2-mercaptoethanol, 0.05M NaCl, 8 mM $MgCl_2$, 10 mM Tris HCl buffer (pH 8.0) including 15 units of the Sfi I restriction enzyme added to every 2 μg of the human DAN. A DNA fragment 121 obtained this way has a structure shown in FIG. 9. In FIG. 9, N can combine with any of the 4 bases. This DNA fragment 121 is bound to fluorescence label DNA 122 having the structure shown in FIG. 9. A 0.02 μm particle is used as a particle 107 containing fluorescein and having carboxyl groups on the surface. This particle contains about 200 molecules of fluorescein. Now, the process of preparing fluorescence label DNA will be described.

A polynucleotide having amino group at the 5' terminus is synthesized by introducing aminolink 2 produced by Applied Biosystems Co. into the final step of the synthesis of a single-stranded polynucleotide having 60 bases. All this synthesis is performed using Applied Biosystems' Model 381 DNA synthesizer in accordance with its instruction manual. The polynucleotide is then bound to the carboxyl group on the surface of the fluorescence particle by means of a water-soluble carbodiimide. Unreactive carboxyl group is regenerated under weakly alkaline conditions. Finally, the hybridization of a complementary DNA chain 3 bases short at the 5' terminus obtains the below DNA bound to the fluorescence particle.

Fluorescence particle-R-CONH-NNNN . . . TGGCCCGCGG-3' 3' - NNNN . . . ACCGGGC -5'

(N: base A, T, G or C, . . . : any polynucleotide) The DNA fragment fuses with the fluorescence-particle-labeled DNA through their association under hybridization conditions and their application to ligase reaction. The above processes obtain DNA 123 having a fluorescence label at one terminus shown in FIG. 9.

Now, the process to introduce a particle into a terminus other than that having a fluorescence label will be described. In this case also, DNA 124 of FIG. 9 bound in advance to a particle fuses with the DNA fragment through ligase reaction. A 1 μm polystyrene particle having carboxyl group on the surface is used. The DNA bound to this particle is prepared in conformity to the production of the above-noted fluorescence-particle-labeled DNA. However, L-lysine is added finally to block unreactive residues. The synthesized DNA bound to the 1 μm particle has a structure like the following:
5' -TGGTGTA . . . NNNN
3' -GGTACCACAT . . . NNNN-R-NHCO-R-particle
(N: base A, T, G or C, . . . : any polynucleotide)

The prepared DNA bound to the particle is used with the particle surface coated with such material as cattle serum albumin or detergent for better dispersion. The particle-bound DNA thus prepared and the DNA fragment having a fluorescence label at one terminus are associated with each other under hybridization conditions and applied to ligase reaction, resulting in a DNA fragment 125 bound to fluorophore at one terminus and to a particle at the other terminus.

Figure 10:
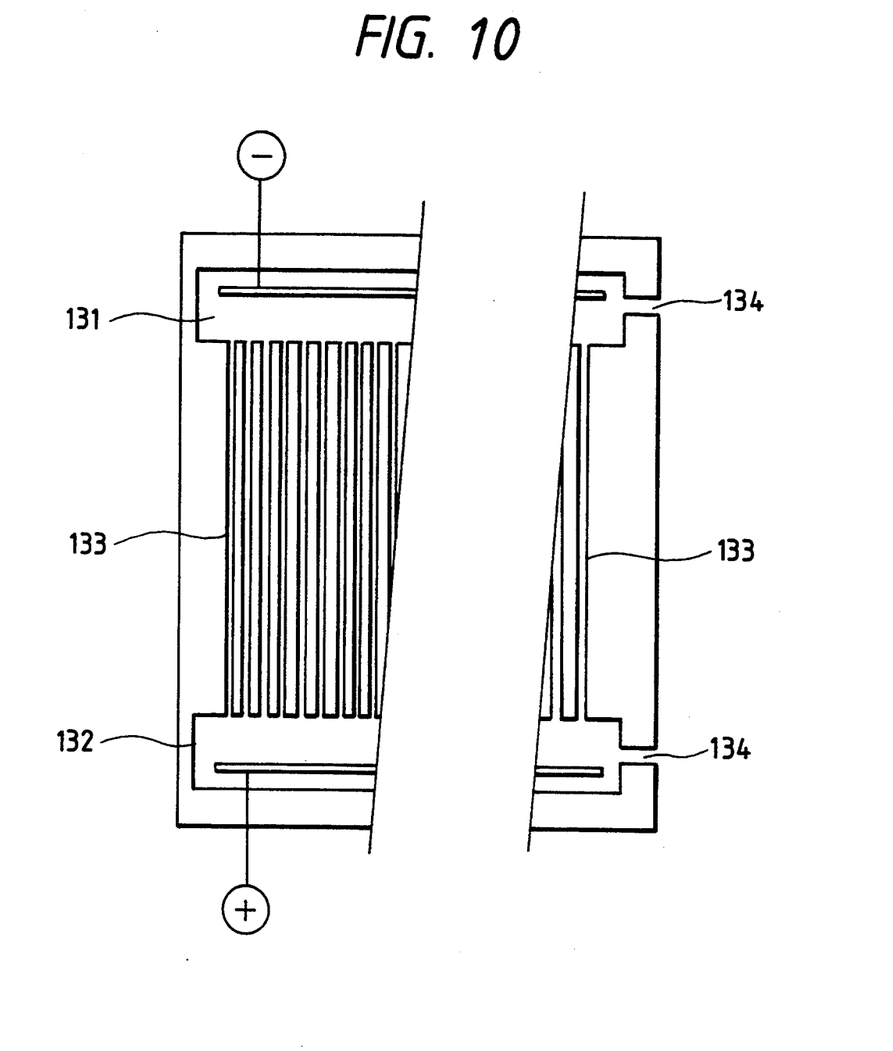
FIG. 10 is a schematic plan view of an embodiment of the present invention illustrating a container for measuring the length of biomoleculars such as DNA.

This DNA fragment bound to fluorophore and a particle was measured using a measuring container shown in FIG. 10. The measuring container is made of nonfluorescent quartz glass, consisting of a sample addition vessel 131 working also as an cathode vessel, an anode vessel 132, about 0.3 μm to 0.8 μm wide apertures 133 and pressure apertures 134. Electric penetration can also be prevented by applying pressure through the pressure apertures 134. The apertures 133 are formed by grooving quartz glass or a silicon wafer and then covering it with quartz glass. Grooves can be made in substrates such as silicon wafers by semiconductor manufacturing techniques using ions, plasma or electron beams. About 0.1 μm deep apertures can usually be made. After the container is filled with a pH 8.0 buffer solution of 89 mM Tris, 89 mM boric acid and 2 mM EDTA2 sodium salt, DNA fragments 125 bound to fluorophore and particles are added to the sample addition vessel 131. When 40 V is applied between the electrode baths, the gathering of most particles (1 μm in diameter) at the aperture mouths is observed with a phase contrast optical microscope. Then, the positions of the fluorophore are found out by means of a confocal laser scanning microscope. About 0.5 μm beams of 488 nm argon laser is directed along the apertures 133. Scattered light is removed, and the resulting fluorescence is applied to photon counting for detection. As a result, 42 fluorescence particles are detected 67 µm away from the fixed particles. The positional standard deviation of detected fluorescence particles is about 1 µm. 8-base-recognition-type restriction enzymes have been used for DNA digestion, so fewer kinds of DNA fragments occur with more selectivity allowed in the binding of fluorophore labels to particles. In this process, therefore, all the human DNA shows fewer kinds of DNA having fluorophore and particles, leading to the advantage of detecting specified DNA with more certainty.

In this example, fluorophore and particles are bound to target DNA by means of ligase reaction, but another process is also possible in which a polynucleotide bound to fluorophore and particles with the series known is allowed to fuse with target DNA through hybridization.

EXAMPLE 6

As in the fifth example, the measurement subject is DNA prepared from human leucocytes.

DNA fragments are digested with the Sfi I restriction enzyme, bound to a fluorescence coloring matter, digested with the Not I restriction enzyme and bound to biotin on the digested terminus surface. This DNA fragment, after being fixed with biotin-avidin reaction, was measured for the distance between its termini by means of a confocal laser scanning microscope.

In accordance with the fifth example, DNA is extracted from human leucocytes, and then DNA fragments resulting from the Sfi I restriction enzyme digestion are bound to 0.05 µm fluorescein-system fluorescence particles. The Not I for 1 unit/µl is allowed to react with the DNA fragments under the conditions of Tris HCl buffer (pH 7.5) containing 100 mM NaCl, 5 mM MgCl 0.01% Triton X-100, 0.5 mM dithiothreitol, 0.1 mg/ml cattle serum albumin. This obtains fluorescence-labeled DNA having one terminus surface resulting from Not I restriction enzyme digestion.

These DNA fragments are then bound to DNA which is bound to fluorescence particles having avidin on the surface. First, preparing the DNA fragments bound to DNA which is bound to fluorescence particles having avidin on the surface will be described from now. Oligo DNA having amino group at the 5' terminus is synthesized, allowed to react with N-hydroxysuccinimidobiotin, made to fuse with a complementary chain through hybridization and mixed with an excessive quantity of avidin-conjugated microparticles. This DNA needs to have a terminus surface resulting from Not I digestion, but, if the other portion is as long as about 10 bases, various structures of the DNA are usable.

Unreactive substances like biotinated oligo DNA are removed by cleaning. The fluorescence particles need to be distinguished from the other termini of the DNA fragments subject to the measurement, that is, from the fluorescence particles on the Sfi I-digested terminus surfaces. For this purpose particles that measure 0.02 µm, contain a rhodamine-like coloring matter and have carboxyl groups on the surface are used as the former fluorescence particles. Avidin is fixed to these particles by the carbodiimide method. The DNA bound to avidin-conjugated microparticles thus prepared is allowed to fuse through hybridization with the previously prepared DNA fragments, and ligase is used for binding the two DNA entities.

Such DNA bound to a fluorescein-like fluorescence particle at one terminus and to an avidin-conjugated microparticle containing a rhodamine-like coloring matter at the other terminus is allowed to react with biotinated quartz glass so as to be fixed. This biotinated quartz glass can be prepared by introducing an amino group into quartz glass in silane coupling reaction and by reaction with N-hydroxysuccinimidobiotin. The DNA fixed this way is then applied to electric fields to be stretched, scanned with 488 nm and 514 nm argon laser, and measured for the positions of the fluorescein-like fluorescence particle and the rhodamine-like fluorescence particle. This results in the recognition of at least 32 µm, 20 µm and 17 µm long DNA. Fixing the DNA in apertures confines its stretching position, so the laser scanning range can be economized. The DNA fragments having one terminus fixed stretch as soon as electric fields are applied to them, so according to the present invention it is possible to measure the length of DNA fragments in a shorter period of time.

As understood from the above, the examples have so far used as samples DNA digested with the restriction enzymes Sfi I and Not I. However, the length of DNA prepared other ways can also be measured by the processes of the present invention. And DNA can be stretched by not only the process using electric fields but also processes like the use of liquid flow.

According to the present invention, as described in the fifth and sixth examples of measuring the length of DNA with one terminus of it fixed, it is not necessary to separate the DNA subject to measurement with electrophoresis, so the length of DNA can be measured in a shorter period of time. Since particles for use in fixing and labeling DNA are not more than 1 µm, DNA not less than tens of µm long can be measured with higher precision. In addition, since stretching DNA through apertures and fine grooves confines the position of the DNA stretching, it is easier to find out labeled termini. Using particles for fixing DNA has the advantage of allowing accurate measurement of the position where the DNA is fixed. According to the present invention, the length of DNA can be measured quickly and accurately, so mutations such as losses or insertions in specific DNA can be recognized.

In any of the above examples of the present invention, the length of DNA most suitable for measurement is 50 kilobases to 6 megabases, but measurement is also possible outside this range.

What is claimed is:

1. A method for measuring the length of a DNA molecule which comprises orienting said DNA molecule into a straight line and transferring said DNA molecule to a buffer solution employing electrophoresis or liquid flow, said DNA molecule being labeled with fluorescence at at least both termini of said DNA molecule, measuring the time interval between the detection of fluorescence emitted from each terminal fluorophore at a predetermined portion irradiated with an excitation light and calculating the distance between the fluorescence labels at both termini from said time interval and a known migration rate of the DNA molecule.

2. A method for measuring the length of a DNA molecule comprising the steps of:

i) labeling at least both termini of said DNA molecule with fluorescence, ii) causing the fluorescence-labeled DNA molecule to migrate by electrophoresis or by liquid flow in a direction toward a buffer solution and orienting the DNA molecule into a straight line, iii) causing the DNA molecule oriented into a straight line to migrate on a path in said buffer solution by electrophoresis or by liquid flow, iv) directing an excitation light beam to a predetermined location on the migration path in said buffer solution, v) detecting fluorescence emitted by a fluorescence label bound to said DNA molecule migrating on said migration path in said buffer solution, said fluorescence label receiving said excitation light beam, vi) measuring the time interval between the detection of fluorescence emitted from each terminal fluorophore, and vii) calculating the distance between the fluorescence labels at both termini from said time interval and a known migration rate of the DNA molecule.

3. A method for measuring the length of a DNA molecule as defined in claim 2 wherein the migration at said steps ii) and iii) is effected by electrophoresis.

4. A method for measuring the length of a DNA molecule which comprises binding a label to one terminus of said DNA molecule, capturing the other terminus physically or chemically at a predetermined position of a matrix having a plurality of grooves or apertures extending in a certain direction, stretching said DNA molecule by means of an electric field or liquid flow and then measuring the distance between the terminal label and the terminus captured with the matrix by detecting the position of said terminal label.

5. A method for measuring the length of a DNA molecule according to claim 4 further comprising binding the other terminus of DNA to a minute particle and then capturing the DNA with the matrix at entrances of a plurality of grooves or apertures each of which is smaller than the minute particle.

6. A method for measuring the length of a DNA molecule according to claim 4 wherein capturing of the DNA in grooves or apertures of a matrix is effected by applying one association reaction selected from the group consisting of immunoreaction, complementary reaction with oligo DNA whose length is known, and reaction in which the biotinylated DNA is immobilized by the interaction of the biotin moiety with an avidin coated particle to the other terminus of the DNA.

7. A method for measuring the length of a DNA molecule according to claim 4 wherein a particle 0.2 $\mu$m to 10 $\mu$m in diameter is bound to the other terminus of DNA.

8. A method for measuring the length of a DNA molecule comprising the steps of:
   i) labeling one terminus of said DNA molecule with fluorescence,
   ii) capturing the other terminus of the DNA molecule at a predetermined position of a matrix having a plurality of grooves or apertures extending in a certain direction,
   iii) stretching said DNA molecule by applying an electric field thereto or placing said DNA molecule in a liquid flow,
   iv) directing an excitation light beam on to said fluorescence label and detecting the fluorescence emitted by said fluorescence label, and
   v) measuring the distance between the terminal label, and the terminus fixed to said matrix by detecting the position of said terminal label.

9. A method for measuring the length of a DNA molecule as defined in claim 8 wherein said step iii) of stretching is effected by applying an electric field.

10. A method for measuring the length of a DNA as defined in claim 9 wherein said step ii) effected by binding a particle to the other terminus of the DNA molecule and fixing the particle to a mouth of one of the grooves or apertures which is smaller than the particle in size.

11. A DNA mapping method which comprises labeling both termini of single-stranded DNA with fluorescence, forming a hybrid with more than one fluorescence label DNA probe at locations other than said termini, orienting said DNA into a straight line, transferring said DNA by electrophoresis or by liquid flow in the direction toward a buffer solution, then measuring each distance between the fluorescence labels by the time interval between each time of detecting the fluorescence emitted from the DNA probes labeled with fluorophore and from both termini of single-stranded DNA labeled with fluorophore and by a known migration rate of the DNA molecule.

12. A method for measuring the length of a DNA molecule which comprises causing a DNA molecule whose termini are both labeled with fluorescence to migrate, while being guided to an area equivalent to an area not more than 10 $\lambda$m in diameter and to become oriented into a straight line and detecting each fluorescence emitted by the fluorescence labels to measure distance between the labels through the time interval of the fluorescence detections and by a known migration rate of the DNA molecule.

13. A method for measuring the length of a DNA molecule comprising the steps of:
   i) labeling at least both termini of said DNA molecule with fluorescence,
   ii) causing the fluorescence-labeled DNA molecule to migrate in electrophoresis gel migration path in the direction toward a buffer solution and orienting the fluorescence-labeled DNA molecule into a straight line,
   iii) transferring the DNA molecule oriented into a straight line from the electrophoresis gel migration path via an outlet not more than 6 $\mu$m in diameter to said buffer solution and maintaining the orientation in a straight line by electrophoresis or liquid flow,
   iv) causing the DNA molecule oriented into a straight line to migrate in a migration path not more than 1 $\mu$m in diameter formed in a sheath flow of said buffer solution with its orientation being kept straight by electrophoresis or by liquid flow,
   v) directing an excitation light beam thinned to a width of not more than 1 $\mu$m to a predetermined location on the migration path in said buffer solution,
   vi) detecting said fluorescence emitted by a fluorescence label bound to said DNA molecule migrating on said migration path in said buffer solution, said fluorescence label receiving said excitation light beam,
   vii) measuring the time interval between the detection of fluorescence emitted from each of the terminal labels, and
   viii) calculating the distance between the fluorescence labels at both termini from said time interval and a known migration rate of the DNA molecule.

* * * * *